US012458521B2

(12) United States Patent
Ryu et al.

(10) Patent No.: US 12,458,521 B2
(45) Date of Patent: Nov. 4, 2025

(54) WEARABLE BOTTOM GARMENT FOR PREVENTING HIP DISLOCATION

(71) Applicant: RS REHAB CO., LTD., Gyeonggi-do (KR)

(72) Inventors: Ju Seok Ryu, Incheon (KR); Jun Chang Lee, Seoul (KR); Young Il Yoon, Sejong (KR); Hyun Jung Han, Chungcheongbuk-do (KR)

(73) Assignee: RS REHAB CO., LTD., Gyeonggi-do (KR)

( * ) Notice: Subject to any disclaimer, the term of this patent is extended or adjusted under 35 U.S.C. 154(b) by 300 days.

(21) Appl. No.: 18/035,927

(22) PCT Filed: Nov. 9, 2020

(86) PCT No.: PCT/KR2020/015622

§ 371 (c)(1),
(2) Date: May 9, 2023

(87) PCT Pub. No.: WO2022/097797

PCT Pub. Date: May 12, 2022

(65) Prior Publication Data

US 2024/0016645 A1 Jan. 18, 2024

(51) Int. Cl.

| | |
|---|---|
| ***A61F 5/01*** | (2006.01) |
| ***A41D 13/05*** | (2006.01) |
| ***A41D 13/12*** | (2006.01) |

(52) U.S. Cl.

CPC ........ *A61F 5/0193* (2013.01); *A41D 13/0506* (2013.01); *A41D 13/1281* (2013.01); *A41D 2400/32* (2013.01)

(58) Field of Classification Search

CPC .............. A61F 5/0193; A41D 13/0506; A41D 13/1281; A41D 2400/32; A61B 5/002;
(Continued)

(56) References Cited

U.S. PATENT DOCUMENTS 1,281,538 A * 10/1918 Nee .......................... A41C 1/00
450/122
3,261,359 A * 7/1966 Gould .................... A41C 1/003
2/67
(Continued)

FOREIGN PATENT DOCUMENTS

| | | |
|---|---|---|
| DE | 202009004817 | 9/2010 |
| ES | 2525507 | 9/2015 |

(Continued)

OTHER PUBLICATIONS

"Search Report of Europe Counterpart Application", issued on Aug. 9, 2024, p. 1-p. 8.

*Primary Examiner* — Tarla R Patel
(74) *Attorney, Agent, or Firm* — JCIPRNET

(57) ABSTRACT

A wearable bottom garment for preventing hip dislocation includes a first strap extending from the upper side of the left hip joint to the lower side of the right hip joint, and a second strap extending from the upper side of the right hip joint to the lower side of the left hip joint, wherein the first strap presses the upper side of the left hip joint from top to bottom, and presses the lower side of the right hip joint from bottom to top, and the second strap presses the upper side of the right hip joint from top to bottom, and presses the lower side of the left hip joint from bottom to top.

7 Claims, 7 Drawing Sheets

(58) Field of Classification Search
CPC ... A61B 5/1114; A61B 5/4571; A61B 5/4836; A61B 5/6804; A61B 5/1107
See application file for complete search history.

(56) References Cited

U.S. PATENT DOCUMENTS

| | | | | |
|---|---|---|---|---|
| 4,862,523 | A * | 9/1989 | Lipov | A41D 31/185 2/409 |
| 6,430,752 | B1 * | 8/2002 | Bay | A41D 1/089 2/228 |
| 7,476,185 | B2 | 1/2009 | Drennan | |
| 8,214,926 | B2 * | 7/2012 | Brown | A61F 5/0104 2/69 |
| 8,435,202 | B2 * | 5/2013 | Lartonoix | A61F 5/0193 602/61 |
| 8,707,463 | B2 * | 4/2014 | Orloff | A63B 21/4009 2/22 |
| 8,951,136 | B1 | 2/2015 | Booher | |
| 9,393,144 | B2 | 7/2016 | Ingimundarson et al. | |
| 2010/0292622 | A1 | 11/2010 | Weissleder et al. | |
| 2014/0165264 | A1 | 6/2014 | Safran et al. | |

FOREIGN PATENT DOCUMENTS

| | | | |
|---|---|---|---|
| JP | 5366059 | | 12/2013 |
| JP | 2015506420 | | 3/2015 |
| JP | 2018201686 | | 12/2018 |
| KR | 2020100009709 | | 10/2010 |
| KR | 1020160071487 | | 6/2016 |
| KR | 2020190000227 | | 1/2019 |
| KR | 101981207 | | 5/2019 |
| KR | 1020210051518 | | 5/2021 |
| KR | 102576593 | B1 * | 9/2023 |
| WO | 2009144877 | | 12/2009 |
| WO | 2013102168 | | 7/2013 |

* cited by examiner

WEARABLE BOTTOM GARMENT FOR PREVENTING HIP DISLOCATION

TECHNICAL FIELD

The present disclosure relates to a wearable bottom garment for preventing hip dislocation, and more particularly, to a wearable bottom garment for preventing hip dislocation by pressing the upper and lower sides of the left and right hip joints through first and second straps respectively extending from the upper sides of the left and right hip joints to the lower sides of the right and left hip joints.

BACKGROUND ART

In general, children with severe cerebral palsy have severe lower limb stiffness due to brain damage, and the stiffness of the adductor muscle is generally more severe than that of the abductor muscle. Due to the stiffness of the adductor muscle, the leg bones of children with cerebral palsy are pulled inward, and the dislocation of a hip joint is promoted according to the principle of leverage applied to the leg bones that are pulled inward.

In detail, referring to FIG. 1, the force of the adductor muscle acts on a leg bone 20 in a direction that brings the legs together to the inside of the legs, and the lever principle is applied to this force, and a force to break away from a hip joint 10 is generated at the end of the leg bone 20. The capsule in the hip joint 10 is torn by the force to break away from the hip joint 10 generated at the end of the leg bone 20, and thus, the dislocation of the hip joint 10 is promoted.

Conventionally, in order to prevent the leg bone 20 from being brought inward, as illustrated in FIG. 2, a fixing bar 30 is used between the leg bones 20. (The fixing bar 30 may be inserted between the legs of a child with cerebral palsy.) As the fixing bar 30 is inserted between the leg bones 20, the force that brings the leg bone 20 inward is resisted, but the use of the fixing bar 30 may rather promote the leverage principle.

In detail, referring to FIG. 2, when the fixing bar 30 is inserted between the leg bones 20, the fixing bar 30 may resist the force that brings the leg bone 20 inward, however the rotational moment rather increases around a position where the fixing bar is inserted. In other words, as the rotational moment generated by the force that brings the leg bone 20 inward due to the adductor muscle is added to the rotational moment generated by the resistance of the fixing bar 30, the force of the leg bone 20 to break away from the hip joint 10 is generated more strongly at an upper end of the leg bone 20. Such an increased rotational moment may rather promote the dislocation of the hip joint 10. (Although the use of the fixing bar 30 resists the force to bring the legs together, this resisting force is rather changed to a force in a direction in which the leg bone 20 rotates around the fixing bar 30. Accordingly, when the fixing bar 30 is used, the dislocation of the hip joint 10 may be rather promoted.)

Conventionally, compression chairs, correction devices, and the like have been used to prevent the dislocation of a hip joint. However, these devices can only be used in a designated space, and there is a problem in that children with cerebral palsy may undergo discomfort due to the use of a specific device, and also, there is insufficient evidence for preventing hip dislocation.

DISCLOSURE

Technical Problem

The present disclosure is directed to solve the problems described above and to provide a wearable bottom garment for preventing hip dislocation through first and second straps respectively extending from the upper sides of the left and right hip joints to the lower sides of the right and left hip joints the upper and lower sides of the left and right hip joints.

Technical Solution

To solve the problems described above, a wearable bottom garment for preventing hip dislocation includes a first strap extending from the upper side of the left hip joint to the lower side of the right hip joint, and a second strap extending from the upper side of the right hip joint to the lower side of the left hip joint, wherein the first strap presses the upper side of the left hip joint from top to bottom, and presses the lower side of the right hip joint from bottom to top, and the second strap presses the upper side of the right hip joint from top to bottom, and presses the lower side of the left hip joint from bottom to top.

To solve the problems described above, the first strap may extend from an upper side with respect to the greater trochanter of the femur of the left hip joint to a lower side with respect to the greater trochanter of the femur of the right hip joint, and the second strap may extend from an upper side with respect to the greater trochanter of the femur of the right hip joint to a lower side with respect to the greater trochanter of the femur of the left hip joint.

To solve the problems described above, the wearable bottom garment for preventing hip dislocation may further include a wearing part worn on both thighs and connected to the first strap and the second strap.

To solve the problems described above, the wearing part may apply a force from inside of the thigh to outside to spread the femurs.

To solve the problems described above, the first strap or the second strap may include the length adjuster for adjusting the length of the first strap or the second strap.

To solve the problems described above, an attachment portion for attaching and detaching one end and the other end of the first strap or the second strap may be provided in the one end and the other end of the first strap or the second strap.

To solve the problems described above, the first strap or the second strap may include a Lycra® material.

To solve the problems described above, the wearable bottom garment for preventing hip dislocation may further include a sensor portion for detecting a state of the legs.

To solve the problems described above, the first strap or the second strap may include a compression portion for tightening the first strap or the second strap.

To solve the problems described above, the compression portion may tighten the first strap or the second strap through data of the state of the legs detected by the sensor portion.

Advantageous Effects

The present disclosure has a merit of preventing the dislocation of a hip joint by surrounding and pressing the upper and lower sides of the left and right hip joints through first and second straps respectively extending from the upper sides of the left and right hip joints to the lower sides of the right and left hip joints.

Furthermore, the present disclosure may improve the effect of preventing dislocation of a hip joint through a wearing part that can apply a force from the inside of thigh to the outside to spread the femurs.

In addition, the present disclosure has an effect of preventing dislocation of a hip joint, without a separate device, by continuously applying a pressure to the upper and lower sides of a hip joint through wearing a wearable bottom garment.

MODE FOR INVENTION

The present specification describes the principle of the disclosure and discloses embodiments to clarify the scope of rights of the disclosure and enable one skilled in the art to which the disclosure pertains to work the disclosure. The disclosed embodiments may be implemented in various forms.

Terms such as “comprise” and/or “may comprise” may be construed to denote a certain function, operation, or constituent element, but may not be construed to exclude the existence of or a possibility of addition of one or more other functions, operations, constituent elements, or the like. Furthermore, in various embodiments of the present disclosure, it is to be understood that the terms such as “including,” “having,” and “comprising” are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

When a constituent element is “connected” or “coupled” to another constituent element, the constituent element contacts or is connected or coupled to the other constituent element directly or through a new other constituent element between the constituent element and the other constituent element. Conversely, when a constituent element is described to be “directly connected” or “directly coupled” to another constituent element, the constituent element should be construed to be directly connected or coupled to another constituent element without any other constituent element interposed therebetween.

The present disclosure relates to a wearable bottom garment for preventing hip dislocation by pressing the upper and lower sides of the left and right hip joints through first and second straps respectively extending from the upper sides of the left and right hip joints to the lower sides of the right and left hip joints.

The wearable bottom garment may be used to prevent the dislocation of a hip joint in a patient with cerebral palsy, but is not limited thereto, and may be applied to a patient having a disease in which the hip joint is dislocated, such as a muscle disease. Hereinafter, preferred embodiments of the present disclosure are described below in detail with reference to the accompanying drawings.

Figure 1:
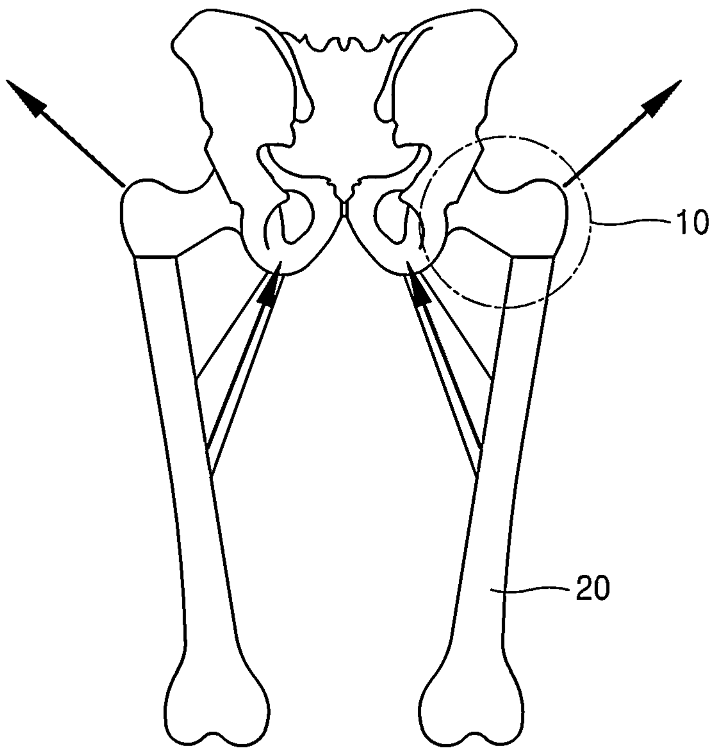
FIG. 1 illustrates the operation of a force generated in a hip joint of a patient with hip dislocation.
Figure 2:
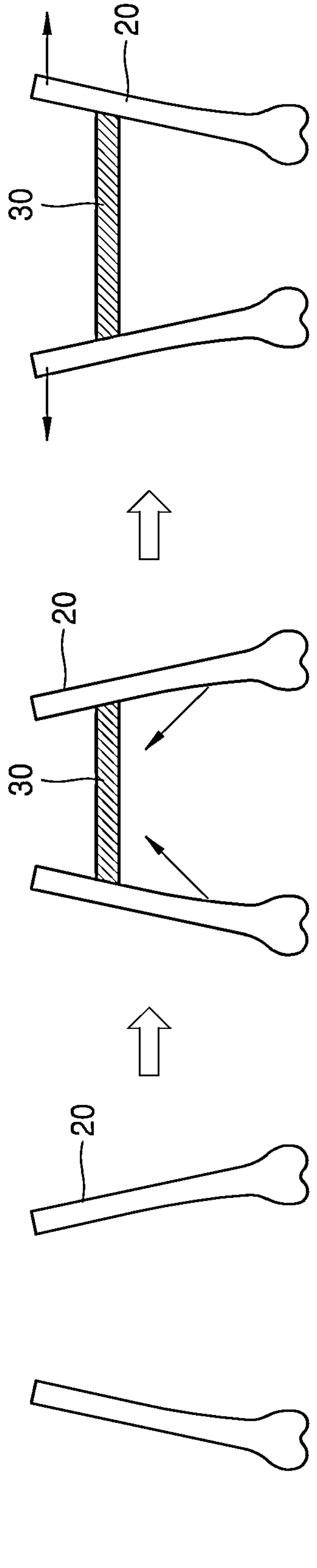
FIG. 2 illustrates the operation of a force generated when a fixing bar is used between leg bones of a patient with hip dislocation.
Figure 3:
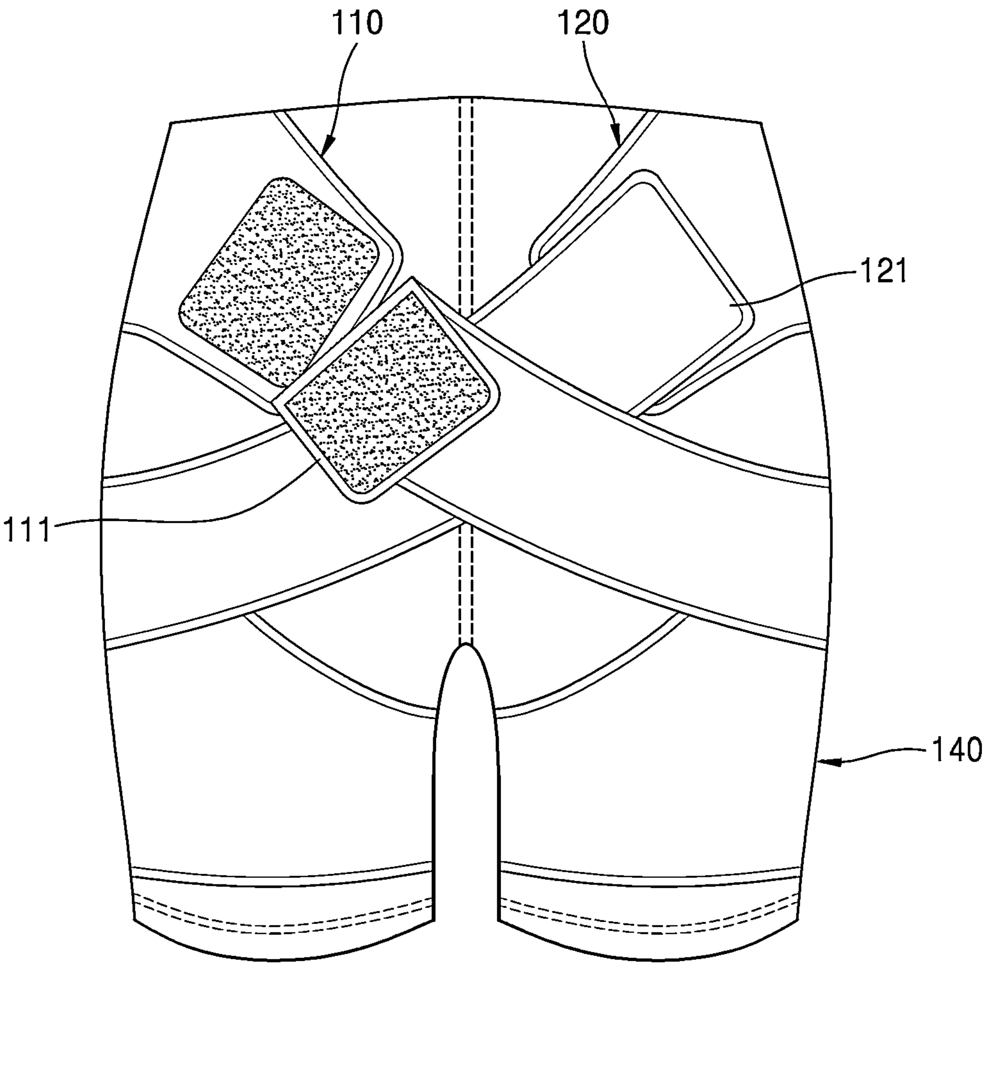
FIG. 3 illustrates a first strap and a second strap of a wearable bottom garment for preventing hip dislocation according to an embodiment of the present disclosure.
Figure 4:
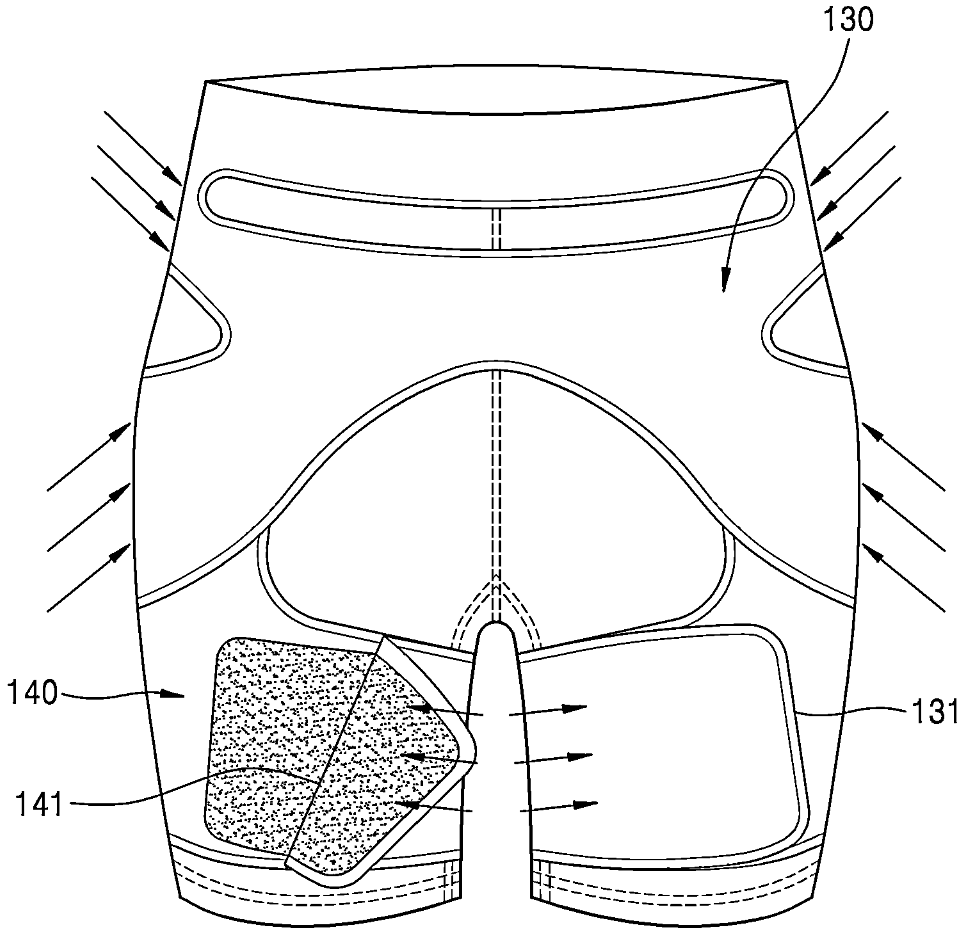
FIG. 4 illustrates a front part and a wearing part of a wearable bottom garment for preventing hip dislocation according to an embodiment of the present disclosure.

Referring to FIGS. 3 and 4, a wearable bottom garment for preventing hip dislocation according to an embodiment of the present disclosure includes a first strap 110 and a second strap 120.

The first strap 110 extends from the upper side of a hip joint 180 at the left to the lower side of a hip joint 180 at the right, and the second strap 120 extends from the upper side of the hip joint 180 at the right to the lower side of the hip joint 180 at the left.

The first strap 110 may press the hip joint 180 from top to bottom in the upper side of the hip joint 180 at the left, and press the hip joint 180 from bottom to top in the lower side of the hip joint 180 at the right. The second strap 120 may press the hip joint 180 from top to bottom in the upper side of the hip joint 180 at the right, and press the hip joint 180 from bottom to top in the lower side of the hip joint 180 at the left.

Figure 5:
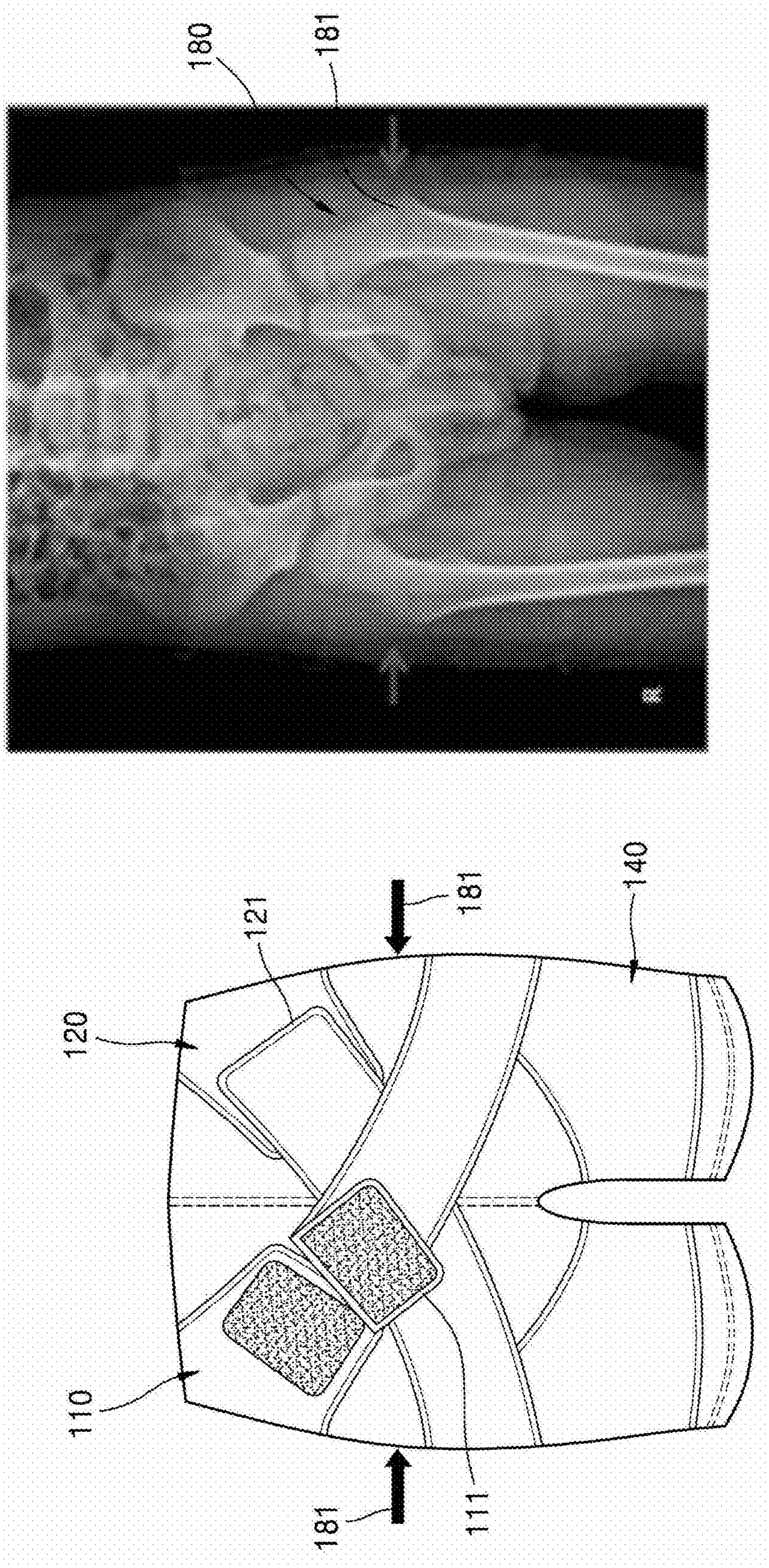
FIG. 5 illustrates that the first and second straps are arranged at the upper and lower sides of the greater trochanter of the femur, according to an embodiment of the present disclosure.

In detail, referring to FIG. 5, the first strap 110 may extend from the upper side with respect to a greater trochanter 181 of the femur of the hip joint 180 at the left, to the lower side with respect to the greater trochanter 181 of the femur of the hip joint 180 at the right, and the second strap 120 may extend from an upper side with respect to the greater trochanter 181 of the femur of the hip joint 180 at the right to a lower side with respect to the greater trochanter 181 of the femur of the hip joint 180 at the left.

In other words, the first strap 110 and the second strap 120 may press the hip joint 180 by surrounding the upper and lower sides with respect to the greater trochanter 181 of the femur of the hip joint 180. As such, when a pressure is applied to the hip joint 180 in the form of surrounding, with a band, the upper and lower sides of the hip joint 180 through the first strap 110 and the second strap 120, a force to allow the hip joint 180 to be detached to the outside may be restricted.

Furthermore, the first strap 110 and the second strap 120 are arranged in the form of surrounding, with a band, the upper and lower sides of the hip joint 180, to assist the function of a capsule encompassing the hip joint 180, thereby preventing the capsule from being torn and preventing the dislocation of the hip joint 180.

The first strap 110 and the second strap 120 may be formed in a band shape, and referring to FIG. 4, the wearable bottom garment for preventing hip dislocation according to an embodiment of the present disclosure may include a front part 130 connecting the first strap 110 with the second strap 120.

The front part 130 may be a part in the form of cloths such that the wearable bottom garment for preventing hip dislocation is to be worn on the human body. The first strap 110 may extend from one side of the front part 130 (the upper side of the hip joint 180 at the left) to the other side of the front part 130 (the lower side of the hip joint 180 at the right), and the second strap 120 may extend from the other side of the front part 130 (the upper side of the hip joint 180 at the right) to one side of the front part 130 (the lower side of the hip joint 180 at the left). As such, a patient is able to wear the wearable bottom garment through the front part 130, the first strap 110, and the second strap 120.

Attachment portions 111 and 121 for facilitating attachment and detachment of one ends and the other ends of the first strap 110 and the second strap 120 may be provided in the one ends and the other ends of the first strap 110 and the second strap 120.

Referring to FIG. 3, the one ends and the other ends of the first strap 110 and the second strap 120 may be separated from each other, and may be attached and detached through the first and second attachment portions 111 or 121. In detail, the first strap 110 may be provided with the first attachment portion 111 formed of Velcro® to allow the one end and the other end of the first strap 110 to be attached to and detached from each other, and the second strap 120 may be provided is the second attachment portion 121 formed of Velcro® to allow the one end and the other end of the second strap 120 to be attached to and detached from each other.

The first and second attachment portions 111 and 121 may be formed of Velcro®, but the disclosure is not limited thereto, and various configurations capable of attaching and detaching the one ends and the other ends of the first strap 110 and the second strap 120 may be used therefor. Furthermore, although the attachment portion may be provided only in any one of the first strap 110 and the second strap 120, providing both of the first strap 110 and the second strap 120 with the first and second attachment portions 111 and 121 is preferable.

As such, when the first strap 110 and the second strap 120 are provided with the first and second attachment portions 111 and 121, the wearability of the wearable bottom garment may be improved, and strength to press the hip joint 180 may be adjusted through the first and second attachment portions 111 and 121.

When the one ends and the other ends of the first strap 110 and the second strap 120 are pulled hard, and then, the one ends and the other ends of the first strap 110 and the second strap 120 are attached to each other through the first and second attachment portions 111 and 121, strong pressure may be applied to the hip joint 180, and when the one ends and the other ends of the first strap 110 and the second strap 120 are pulled lightly, and then, the one ends and the other ends of the first strap 110 and the second strap 120 are attached to each other through the first and second attachment portions 111 and 121, light pressure may be applied to the hip joint 180.

Furthermore, as described above, when the first strap 110 and the second strap 120 are respectively provided with the first and second attachment portions 111 and 121, pressing positions may be selectively set in the upper and lower sides of the hip joint 180 and pressed, and accordingly, indigestion, skin chafing, and the like may be prevented in advance by reducing pressure on the stomach and groin.

Figure 6:
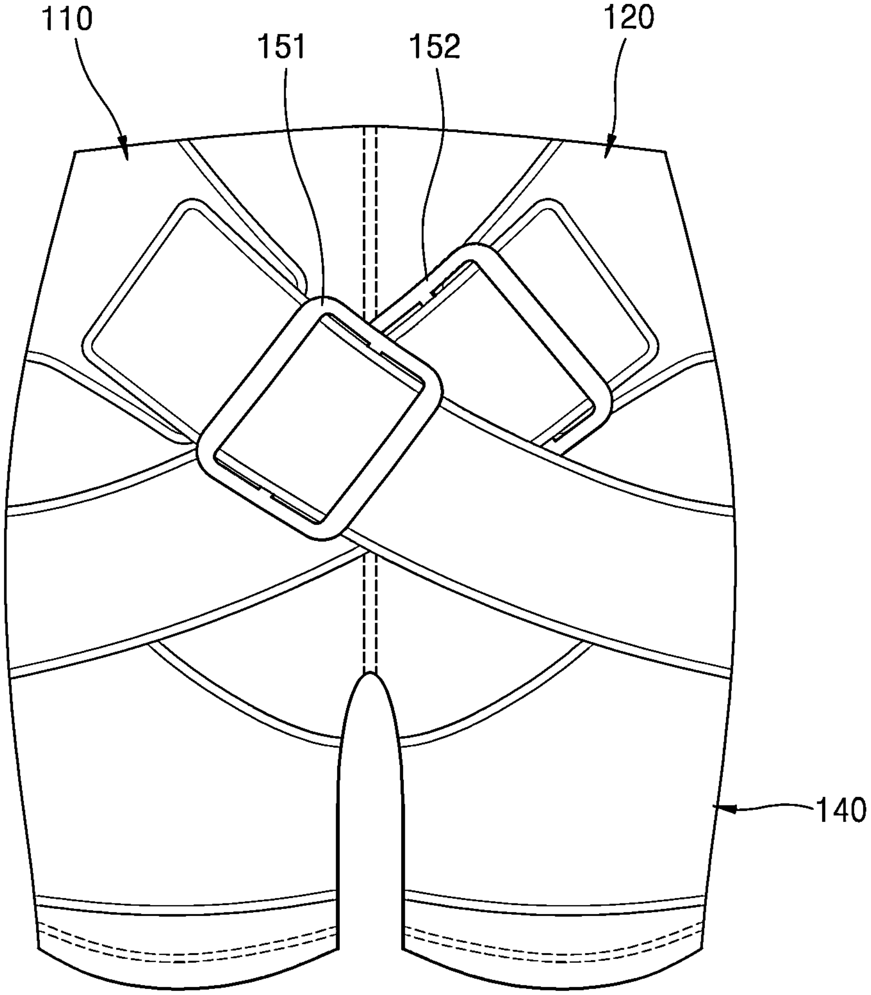
FIG. 6 illustrates that a length adjuster is provided on the first and second straps, according to an embodiment of the present disclosure.

Referring to FIG. 6, the first strap 110 or the second strap 120 according to an embodiment of the present disclosure may be provided with length adjusters 151 and 152 for controlling the length of the first strap 110 or the second strap 120.

The first strap 110 may be provided with the first length adjuster 151 for controlling the length of the first strap 110, and the second strap 120 may be provided with the second length adjuster 152 for controlling the length of the second strap 120.

The length adjusters 151 and 152 are capable of adjusting the lengths of the first strap 110 and the second strap 120, and various configurations capable of adjusting the lengths of the first strap 110 and the second strap 120 may be used therefor.

For example, buckles capable of adjusting the length of a strap by inserting the strap may be used as the length adjusters 151 and 152. However, the length adjusters 151 and 152 are not limited thereto, and various configurations capable of adjusting the lengths of the first strap 110 and the second strap 120 may be used therefor.

As such, when the first strap 110 and the second strap 120 are provided with the length adjusters 151 and 152, the wearability of the wearable bottom garment may be improved, and the strength to press the hip joint 180 may be adjusted through the first and second attachment portions 111 and 121.

In detail, user's wearability may be improved by increasing the lengths of the first strap 110 and the second strap 120 through the length adjusters 151 and 152. Furthermore, strong pressure may be applied to the hip joint 180 by tightening the first strap 110 and the second strap 120 through the length adjusters 151 and 152, and light pressure may be applied to the hip joint 180 by loosely pulling the first strap 110 and the second strap 120 through the length adjusters 151 and 152.

The first strap 110 and the second strap 120 may be provided with all of the length adjusters 151 and 152 and the first and second attachment portions 111 and 121, or the length adjusters 151 and 152 and the first and second attachment portions 111 and 121 may be selectively provided. Furthermore, although the length adjuster may be provided only in any one of the first strap 110 and the second strap 120, the length adjusters 151 and 152 are preferably provided in both of the first strap 110 and the second strap 120.

Although, as described above, the first strap 110 and the second strap 120 are provided in the first and second attachment portions 111 and 121 and the length adjusters 151 and 152, the disclosure is not limited thereto. The first strap 110 and the second strap 120 may be integrally formed without having the first and second attachment portions 111 and 121 and the length adjusters 151 and 152, the first strap 110 and the second strap 120 may be provided with a different device.

The wearable bottom garment for preventing hip dislocation according to an embodiment of the present disclosure may further include a wearing part 140 connected to the first strap 110 and the second strap 120 and worn on both thighs.

Referring to FIG. 3, the wearing part 140 may be connected to the first strap 110 and the second strap 120 and worn on both thighs. The wearing part 140 may be connected directly to the first strap 110 and the second strap 120, and indirectly thereto through the front part 130.

When the wearing part 140 are worn on both thighs, it is preferable for the wearing part 140 to apply a force from the inside of thigh to the outside to spread the femurs.

As the adductor muscle of a hip joint stiffens hard and the abductor muscle is relatively weak, coxa valga and anteversion are increased. When a force is applied from the inside of thigh to the outside through the wearing part 140, the stiffness of the adductor muscle of a hip joint is reduced and the contraction of the abductor muscle of a hip joint is encouraged so that the dislocation of a hip joint may be prevented. Furthermore, as pressure is applied to the upper and lower sides of the greater trochanter of the femur, coxa valga may be reduced.

In other words, as the upper and lower sides of the hip joint 180 are pressed through the first strap 110 and the second strap 120, and a force is applied from the inside of thigh to the outside through the wearing part 140 to spread the femurs, the dislocation of a hip joint may be further prevented.

To apply a force from the inside of thigh to the outside through the wearing part 140, the wearing part 140 may be provided with a third attachment portion 141. In the wearing part 140, one end and the other end of a portion surrounding each thigh may be separated from each other. In the wearing part 140, the one end and the other end of the portion surrounding each thigh may be attached to and detached from each other through the third attachment portion 141.

Referring to FIG. 4, the third attachment portion 141 may be attached through Velcro® while surrounding each thigh from the inside to the outside. As such, while the third attachment portion 141 surrounds each thigh from the inside to the outside and is attached through Velcro®, a force may be applied from the inside of thigh to the outside.

Although the third attachment portion 141 is described as being attached through Velcro®, the disclosure is not limited thereto, and in the wearing part 140, various configurations capable of attaching and detaching the one end and the other end of the portion surrounding each thigh and applying a force from the inside of thigh to the outside may be used.

Furthermore, the wearing part 140 may include fibers, and the direction of the fibers included in the wearing part 140 is configured to be pulled from the inside of thigh to the outside, thereby applying a force from the inside of thigh to the outside. (The direction of the fibers of the wearing part 140 may be arranged parallel to a direction from the inside of thigh to the outside, and the fibers are elastically pressed when the wearing part 140 is worn on the thigh, and may apply a force from the inside of thigh to the outside.)

The first strap 110, the second strap 120, the front part 130, and the wearing part 140 according to the embodiment of the present disclosure described above may include a Lycra® material. The Lycra® material, which is an elastic material, may closely adhere to the human body, such as a swimsuit or cycle clothes, and transmit an elastic pressing force to the human body.

However, the materials for the first strap 110, the second strap 120, the front part 130, and the wearing part 140 are not limited thereto, and various materials may be used therefor. Furthermore, the first strap 110, the second strap 120, the front part 130, and the wearing part 140 may include the same material, but include different materials as necessary.

Figure 7:
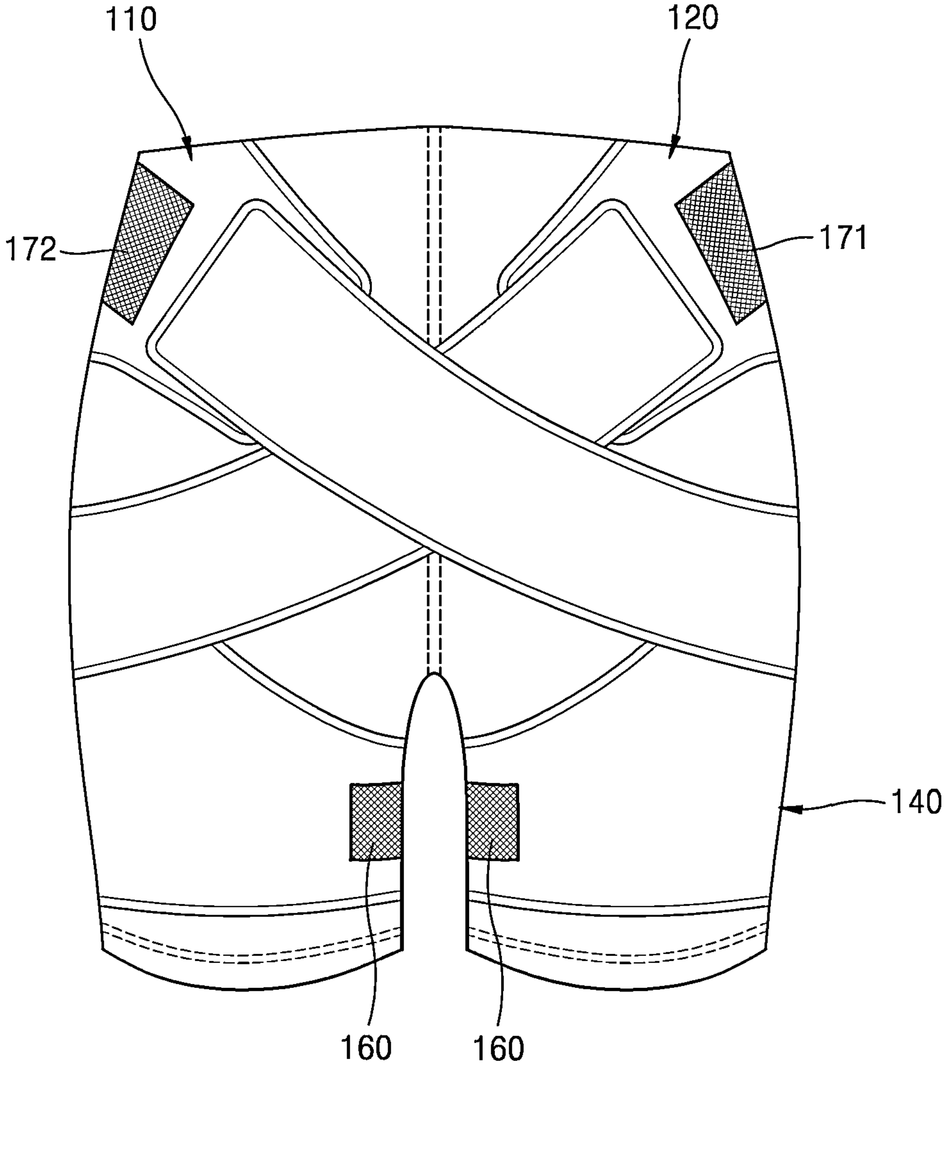
FIG. 7 illustrates a sensor portion and a compression portion of a wearable bottom garment for preventing hip dislocation according to an embodiment of the present disclosure.

Referring to FIG. 7, the wearable bottom garment for preventing hip dislocation of the present disclosure may further include a sensor portion 160 and compression portions 171 and 172.

The sensor portion 160 may sense the state of the legs. In detail, the sensor portion 160 may detect contraction and relaxation of thigh muscles and stiffness of the thigh muscles in the leg, and may detect contraction and relaxation of some of the muscles of the leg and stiffness of the muscles.

Furthermore, the sensor portion 160 may detect the movement of the legs (the direction to bring the legs together, etc.), the inclination of the legs, and the like, and may include various types of sensors capable of detecting the state of the legs.

Referring to FIG. 7, the sensor portion 160 is provided in the wearing part 140 and detects the state of the legs. However, the disclosure is not limited thereto, and the sensor portion 160 may be provided at various positions. For example, the sensor portion 160 may be provided at any one of the first strap 110, the second strap 120, and the front part 130.

The compression portions 171 and 172 may be provided in the first strap 110 or the second strap 120, and the compression portions 171 and 172 may tighten the first strap 110 or the second strap 120. Various devices capable of tightening the first strap 110 or the second strap 120 and applying a pressure to the hip joint 180 may be used as the compression portions 171 and 172.

For example, the compression portions 171 and 172 may be provided in the length adjusters 151 and 152, and the compression portions 171 and 172 may, in response to a signal, reduce the length of the first strap 110 or the second strap 120 and also tighten the first strap 110 or the second strap 120.

Preferably, when the first strap 110 or the second strap 120 is worn on the human body, the compression portions 171 and 172 may be arranged to tighten the hip joint from the side surface of the human body. In detail, the compression portions 171 and 172 may be arranged at positions surrounding the hip joint 180 in the first strap 110 or the second strap 120.

When the first strap 110 or the second strap 120 is worn on the human body, and the compression portions 171 and 172 are arranged in the front side of the human body, friction of a strap may be generated between the first strap 110 or the second strap 120 and the human body. In this case, due to the friction of a strap, the hip joint may not be normally tightened through the first strap 110 or the second strap 120.

Accordingly, when the first strap 110 or the second strap 120 is worn on the human body, the compression portions 171 and 172 may be arranged to tighten the hip joint from the side of the human body, and the compression portions 171 and 172 may be arranged at positions surrounding the hip joint 180 in the first strap 110 or the second strap 120.

However, the positions of the compression portions 171 and 172 are not limited thereto, and the compression portions 171 and 172 may be arranged at various positions of the first strap 110 and the second strap 120. Furthermore, various devices capable of tightening the first strap 110 or the second strap 120 may be used as the compression portions 171 and 172.

The first strap 110 may be provided with the first compression portion 171, and the second strap 120 may be provided with the second compression portion 172. Although the compression portion may be provided in any one position of the first strap 110 and the second strap 120, the compression portion may be provided in both of the first strap 110 and the second strap 120.

The compression portions 171 and 172 may tighten the first strap 110 or the second strap 120 through data of the state of the legs detected by the sensor portion 160.

The legs of a patient with hip dislocation are generally moved in a direction in which the legs are put together as the adductor muscle inside the hip joint contacts and the legs cross each other. In addition, a patient with hip dislocation may exhibit a leg movement of a specific state.

The sensor portion 160 may detect a leg movement appearing in a patient with hip dislocation, and through the data of the state of the legs detected by the sensor portion 160, the hip joint 180 may be tightened and pressed by the first strap 110 and the second strap 120 from the upper and lower sides of the hip joint 180.

Although any one of the first strap 110 and the second strap 120 may be tightened through the state date of the legs detected by the sensor portion 160, the first strap 110 and the second strap 120 may be simultaneously tightened.

According to an embodiment of the present disclosure, the sensor portion 160 and the compression portions 171 and 172 may be electrically connected to each other in a wired or wireless manner. Furthermore, a controller for receiving data of the sensor portion 160 and transmitting the data to the compression portions 171 and 172 may be further provided, and the operations of the sensor portion 160 and the compression portions 171 and 172 may be controlled by the controller.

The wearable bottom garment for preventing hip dislocation according to an embodiment of the present disclosure described above has the following effects.

The wearable bottom garment for preventing hip dislocation according to an embodiment of the present disclosure may prevent dislocation of a hip joint by pressing the hip joint in the form of surrounding the upper and lower sides of the left and right hip joints, through the first and second straps respectively extending from the upper sides of the left and right hip joints to the lower sides of the right and left hip joints dislocation of a hip joint.

Furthermore, the wearable bottom garment for preventing hip dislocation according to an embodiment of the present disclosure may improve the effect of preventing the dislocation of a hip joint through the wearing part that can apply a force from the inside of the thigh to the outside to spread the femurs.

Furthermore, the wearable bottom garment for preventing hip dislocation according to an embodiment of the present disclosure may improve the effect of preventing dislocation of a hip joint by detecting the contraction of thigh muscle through the sensor portion and tightening the first and second straps through the compression portion.

In addition, the wearable bottom garment for preventing hip dislocation according to an embodiment of the present disclosure has an effect of preventing dislocation of a hip joint, without a separate device, by continuously applying a pressure to the upper and lower sides of a hip joint through wearing a wearable bottom garment.

While the disclosure has been particularly shown and described with reference to preferred embodiments using specific terminologies, the embodiments and terminologies should be considered in descriptive sense only and not for purposes of limitation. Therefore, it will be understood by those of ordinary skill in the art that various changes in form and details may be made therein without departing from the spirit and scope of the disclosure as defined by the following claims.

The invention claimed is:

1. A wearable bottom garment to be worn on legs for preventing hip dislocation, the wearable bottom garment comprising:

a first strap extending from an upper side of a left hip joint to a lower side of a right hip joint;

a second strap extending from an upper side of the right hip joint to a lower side of the left hip joint; and a wearing part worn on both thighs and connected to the first strap and the second strap, wherein the first strap presses the upper side of the left hip joint from top to bottom and the lower side of the right hip joint from bottom to top, and the second strap presses the upper side of the right hip joint from top to bottom and the lower side of the left hip joint from bottom to top, wherein the wearing part applies a force from inside of the thigh to outside to spread the femurs, wherein the wearing part includes fibers, wherein a direction of the fibers of the wearing part is arranged parallel to a direction from the inside of thigh to the outside and the force is applied from the inside of thigh to the outside.

2. The wearable bottom garment of claim 1, wherein the first strap extends from an upper side with respect to a greater trochanter of a femur of the left hip joint to a lower side with respect to a greater trochanter of a femur of the right hip joint, and the second strap extends from an upper side with respect to the greater trochanter of the femur of the right hip joint to a lower side with respect to the greater trochanter of the femur of the left hip joint.

3. The wearable bottom garment of claim 1, wherein the first strap or the second strap comprises a length adjuster for adjusting a length of the first strap or the second strap.

4. The wearable bottom garment of claim 1, wherein an attachment portion for attaching and detaching one end and the other end of the first strap or the second strap is provided in the one end and the other end of the first strap or the second strap.

5. The wearable bottom garment of claim 1, further comprising a sensor portion for detecting a state of the legs.

6. The wearable bottom garment of claim 5, wherein the first strap or the second strap comprises a compression portion for tightening the first strap or the second strap.

7. The wearable bottom garment of claim 6, wherein the compression portion tightens the first strap or the second strap through data of the state of the legs detected by the sensor portion.

* * * * *